(12) United States Patent
McNutt et al.

(10) Patent No.: US 6,735,277 B2
(45) Date of Patent: May 11, 2004

(54) INVERSE PLANNING FOR INTENSITY-MODULATED RADIOTHERAPY

(75) Inventors: Todd R. McNutt, Verona, WI (US); R. Keith Tipton, Verona, WI (US); R. Terry Ward, Madison, WI (US); Scott L. Johnson, Madison, WI (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 162 days.

(21) Appl. No.: 10/154,135

(22) Filed: May 23, 2002

(65) Prior Publication Data

US 2003/0219098 A1 Nov. 27, 2003

(51) Int. Cl.$^7$ .............................................. A61N 5/10
(52) U.S. Cl. ........................................... 378/65; 378/64
(58) Field of Search .............................. 378/64, 65, 901

(56) References Cited

U.S. PATENT DOCUMENTS

| | | | | |
|---|---|---|---|---|
| 5,802,136 A | 9/1998 | Carol | ........................... | 378/65 |
| 5,818,902 A | 10/1998 | Yu | ............................... | 378/65 |
| 6,049,587 A | 4/2000 | Leksell et al. | ................. | 378/65 |
| 6,240,161 B1 | 5/2001 | Siochi | ......................... | 378/65 |
| 6,260,005 B1 | 7/2001 | Yang et al. | .................... | 703/11 |
| 2002/0051513 A1 * | 5/2002 | Pugachev et al. | .............. | 378/65 |
| 2002/0106054 A1 * | 8/2002 | Caflisch et al. | ................ | 378/65 |
| 2003/0068009 A1 * | 4/2003 | Xing | ............................ | 378/65 |

OTHER PUBLICATIONS

Oldham, et al., "Intensity–Modulated Radiotherapy By Means of Static Tomotherapy: A Planning & Verification Study", Med. Phys. 24 (6) Jun. 1997 XP–000767837.

* cited by examiner

Primary Examiner—David V Bruce
(74) Attorney, Agent, or Firm—Eugene E. Clair, Esq.

(57) ABSTRACT

A radiation treatment apparatus (10) includes a diagnostic imaging scanner (12) that acquires a diagnostic image of a subject. A contouring processor (54) computes a radiation treatment objective based thereon. A radiation delivery apparatus (60) delivers radiation to the subject. An inverse planning processor (80) computes radiation beamlet parameters conforming with the radiation treatment objective by: grouping the beamlet parameters; assigning a weight to each group (82, 84, 86); optimizing a first group (82) to produce an intermediate dosage objective corresponding to the treatment objective weighted by a weight of the first group (82); and optimizing successive groups (84) to produce with the previously optimized groups (82) an increasing intermediate dosage objective corresponding to the treatment objective weighted by the combined weights of the previous and current groups (82, 84). A conversion processor (90) converts the optimized beamlet parameters into configuration parameters of the radiation delivery apparatus (60).

21 Claims, 4 Drawing Sheets

INVERSE PLANNING FOR INTENSITY-MODULATED RADIOTHERAPY

BACKGROUND OF THE INVENTION

The present invention relates to the irradiating arts. It particularly relates to radiation treatment of a subject using spatially intensity-modulated radiation to deliver targeted and controlled dosage distributions, and will be described with particular reference thereto. However, the invention will also find application in conjunction with controlled delivery of radiation for other applications such as diagnostic imaging as well as in other radiation absorption analyses such as computation of light absorption for optical modeling.

Oncological radiation therapy (sometimes called radiotherapy) is used for controlling, reversing, or sometimes even eliminating cancerous growths. Ionizing radiation such as high energy photons (e.g., x-rays or gamma rays), proton or neutron particles, or the like are applied to a cancerous tumor or other cancerous region. The ionizing radiation damages cellular DNA which can kill irradiated cells. Because growing and rapidly multiplying cancer cells are typically more readily damaged by the radiation and less able to repair such damage than are healthy cells, there is usually a beneficially built-in selectivity favoring elimination of cancerous tissue and survival of healthy tissue.

However, irradiated healthy tissue is usually also damaged by the radiotherapy to at least some extent, and such radiation damage can produce highly detrimental side-effects to the therapy which are preferably minimized or avoided. To reduce damage to healthy tissue, radiotherapy typically includes a series of treatments performed over an extended period of time e.g., over several weeks. Serial treatment facilitates beneficial repair of damaged non-cancerous cells between treatments.

Another approach for maximizing the beneficial cancer-killing effect of radiotherapy while minimizing damage to healthy cells is intensity modulated radiotherapy (IMRT). The IMRT technique employs a plurality of radiation beams applied to the target area simultaneously or sequentially at several angles or orientations. The spatial beam intensity profile is controlled using multi-leaf collimators or other beam-shaping elements known to the art, such that the cumulative dosage delivered to the target area is controlled to produce a selected radiation dosage profile that targets cancerous regions or tumors while minimizing the radiation dosage to neighboring critical structures.

A variation on the IMRT method is tomotherapy. This method uses a geometry similar to that of helical computed tomography (CT). A linear electron accelerator, or linac, is mounted on a rotating gantry that rotates the beam aperture about the subject while linearly moving the subject in a direction perpendicular to the plane of source rotation. This effectuates a helical orbit of the beam aperture about the subject. During helical orbiting, the beam is selectively controlled to deliver a selected radiation dosage profile to the target area. Optionally, a tungsten or other target is inserted in the beam path, which intercepts the accelerated electrons and emits photons, e.g. x-rays or gamma rays, which irradiate the target area.

Determination of appropriate radiotherapy parameters for delivering a selected radiation dosage profile is a complex task. Usually, planning images of the target area are acquired using computed tomography (CT) or another diagnostic imaging technique. CT beneficially provides both structural information and radiation attenuation or tissue density information which is used in determining radiotherapy radiation absorption profiles. IMRT planning can include optimizing as many as ten thousand beam parameters, while planning for tomotherapy is even more complex due to the continuous helical orbit of the radiation aperture, and can include optimizing around sixty thousand parameters.

The present invention contemplates an improved apparatus and method which overcomes the aforementioned limitations and others.

SUMMARY OF THE INVENTION

According to one aspect of the invention, a method is provided for delivering to a subject a selected radiation treatment described by a treatment radiation dosage distribution objective. The delivering includes application of at least one intensity-modulated beam whose radiation output is described by a plurality of beamlet parameters. The beamlet parameters are divided into a plurality of groups, each group including one or more beamlet parameters. A group weighting is assigned to each group based at least on a fraction of the beamlet parameters included in the group. A first group is selected. A first intermediate radiation dosage distribution objective is computed based on the treatment radiation dosage distribution objective and the first group weighting. The first group of beamlet parameters is optimized respective to the first intermediate radiation dosage distribution objective. A next group is selected. A second intermediate radiation dosage distribution objective is determined based on the treatment radiation dosage distribution objective and the next group weighting. The next group of beamlet parameters is optimized respective to the second intermediate radiation dosage distribution objective. The next group selection, second intermediate objective determination, and next group optimization steps are repeated to optimize all the beamlet intensity parameters. The optimized beamlet intensity parameters are converted to a deliverable sequence of radiation fields. Then at least one intensity-modulated beam is applied to effectuate the deliverable sequence.

According to another aspect of the invention, a radiation treatment apparatus is disclosed for delivering a radiation treatment to a subject. A diagnostic imaging scanner acquires a diagnostic image of a target area of the subject. A contouring processor computes a radiation treatment objective based on the diagnostic image. A radiation delivery apparatus is configured to deliver the radiation treatment objective to the subject. The radiation produced by the radiation delivery apparatus during the radiation treatment is representable as a plurality of parameterized beamlets. An inverse planning processor computes beamlet parameters conforming with the radiation treatment objective. The inverse planning processor performs a method including: grouping the beamlet parameters into a plurality of groups each including one or more beamlet parameters; assigning a contribution weight to each beamlet parameter group; optimizing a first beamlet parameter group with respect to a first intermediate target dosage objective corresponding to the radiation treatment objective weighted by the contribution weight of the first beamlet parameter group; and optimizing successive beamlet parameter groups with respect to a second intermediate target dosage objective weighted by at least the contribution weight of at least the currently optimized beamlet parameter group. A conversion processor converts the optimized beamlet parameters into configuration parameters of the radiation delivery apparatus.

According to yet another aspect of the invention, an apparatus is disclosed for delivering to a subject a selected radiation treatment described by a treatment radiation dosage distribution objective. The delivering includes application of at least one intensity-modulated beam whose radiation output is described by a plurality of beamlet parameters. A grouping means is provided for dividing the beamlet parameters into a plurality of groups, each group including one or more beamlet parameters. A weighting means is provided for assigning a group weighting for each group based at least on a fraction of the beamlet parameters included in the group. A means is provided for computing an intermediate radiation dosage distribution objective based on the treatment radiation dosage distribution objective and combined weightings of one or more selected groups. An optimizing means is provided for optimizing the beamlet parameters of a current group respective to the intermediate radiation dosage distribution objective. A looping means is provided for successively applying the means for computing an intermediate radiation dosage distribution objective and the optimizing means to determine optimized values for the beamlet parameters of each group. A converting means is provided for converting the optimized beamlet intensity parameters to a deliverable sequence of radiation fields. A radiation delivery means is provided for applying at least one intensity-modulated beam to effectuate the deliverable sequence.

One advantage of the present invention resides in improved speed in computing parameters for delivering a selected radiation treatment objective.

Another advantage of the present invention resides in reduced computational load during radiation treatment planning.

Yet another advantage of the present invention resides in substantially reducing the complexity of parameter optimization processing in tomotherapy planning.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
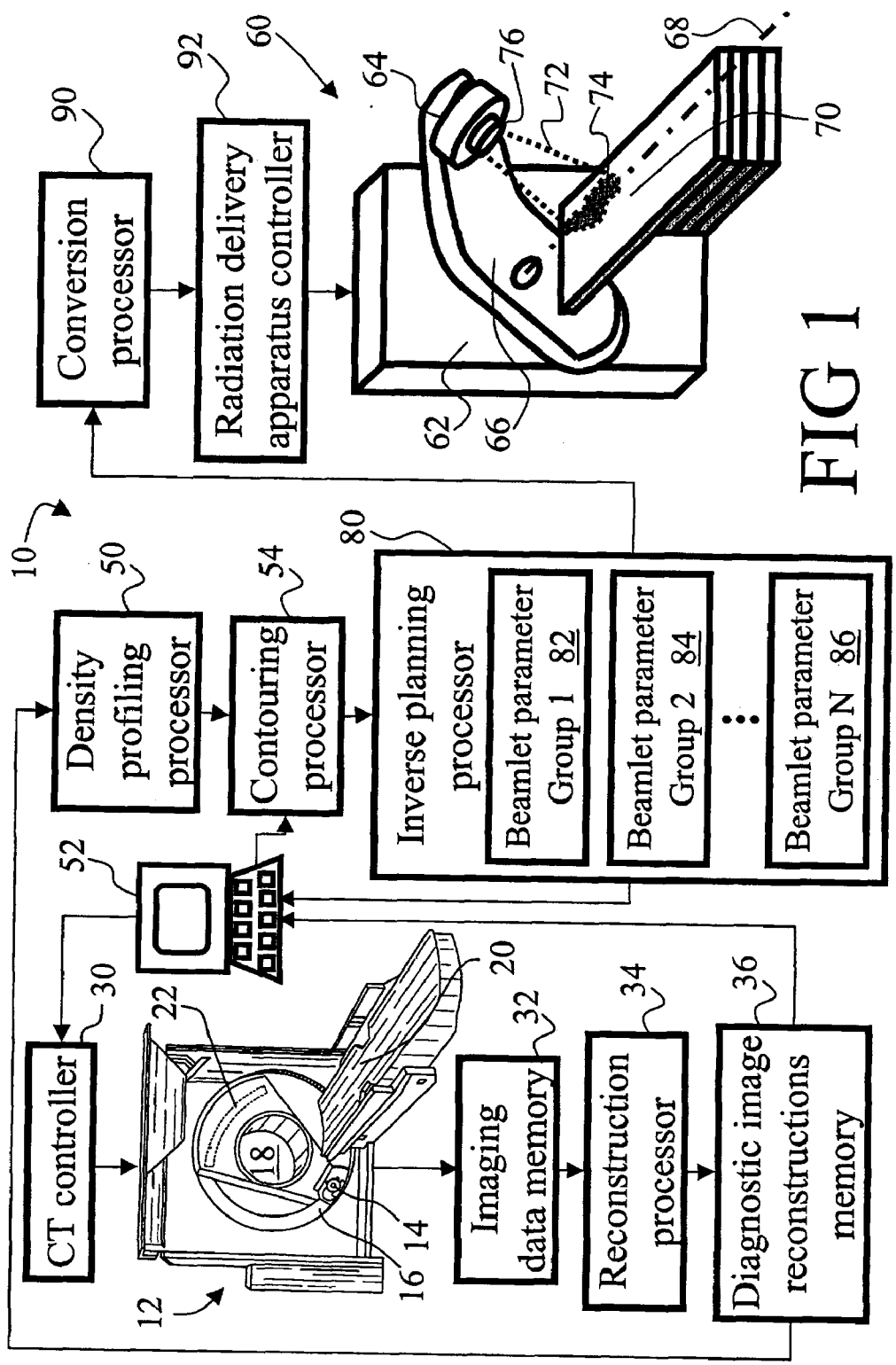
FIG. 1 schematically shows an exemplary radiation therapy apparatus in accordance with an embodiment of the invention.

With reference to FIG. 1, a radiation therapy system 10 includes a computed tomography (CT) imaging scanner 12 for obtaining diagnostic images for use in planning the radiation therapy treatment. The CT imaging scanner 12 includes an x-ray source 14 mounted on a rotating gantry 16. The x-ray source 14 produces a fan- or cone-beam of x-rays passing through an examination region 18, where they interact with a target area of a subject (not shown) supported by a support 20 which linearly moves the target area within the examination region 18. The linear subject movement cooperates with rotation of the x-ray source 14 by the gantry 16 to produce a helical orbiting of the x-ray source 14 relative to the subject. An x-ray detector array 22 is arranged to receive the x-ray beam after it passes through the examination region 18 where the x-rays interact with and are partially absorbed by the subject. The detected x-rays therefore include absorption information relating to the subject.

The CT scanner 12 is operated by a CT controller 30 to perform selected imaging sequences of a selected target area of the subject which is to be treated by radiotherapy. The imaging sequences acquire diagnostic imaging data of the target area. The diagnostic imaging data is stored in an imaging data memory 32. A reconstruction processor 34 reconstructs image representations from the acquired imaging data, and the reconstructed image representations are stored in a diagnostic image reconstructions memory 36.

The described diagnostic imaging sub-system is exemplary only. Those skilled in the art will recognize that the helical cone-beam CT scanner 12 is optionally replaced by a single-slice or a multi-slice fan-beam CT scanner or other type of CT imaging scanner. Furthermore, other types of diagnostic imaging scanners, such as a magnetic resonance imaging (MRI) scanner, a positron emission tomography (PET) scanner, a single photon emission computed tomography (SPECT) scanner, or the like can be substituted for the CT scanner 12.

With continuing reference to FIG. 1, the diagnostic imaging apparatus 12 is separate from a radiotherapy delivery sub-system 60. Preferably, fiduciary markers are applied to the subject prior to the diagnostic imaging, and remain in place until the subsequent radiotherapy to provide registration between the diagnostic images and the radiotherapy delivery. Other methods for spatial registering between diagnostic image acquisition and the radiotherapy are also contemplated, such as using intrinsic anatomical markers. Furthermore, it is also contemplated to integrate the diagnostic imaging scanner with the radiotherapy apparatus to reduce misregistration between the diagnostic imaging and the radiotherapy.

With continuing reference to FIG. 1, a density profiling processor 50 computes a physical density of structures in and around a target area of the subject designated on an operator console 52. The target and critical structures are manually located on displays of the diagnostic image reconstructions. Alternatively, the various areas are determined automatically based on density or other characteristics. The physical density is used for computing absorption or attenuation of the radiation used in the radiotherapy as it passes into and through the subject.

A contouring processor 54 defines regions of interest for radiation therapy including the target, critical structures in which radiation dosage is to be minimized within the target area, radiation blocking structures, and the like. The contours are drawn manually on the console. Preferably, the boundaries are refined electronically by automatically located density interfaces. Alternately, the regions of interest are identified automatically from density or other characteristics which differentiate the regions from each other and from other tissue in the electronic image representation. As yet another option, the operator designates one or a small number of seed points in each region and the density profiling processor 50 grows the points to define regions that incorporate surrounding voxels of the same density or having other distinguishing characteristics. Typically, the contouring processor 54 provides a radiation treatment objective which includes a target radiation dosage distribution within the target area. Optionally, constraints are also included in the radiotherapy objective, such as maximum radiation dosages in selected critical structures.

For example, a radiation dosage of 80 Gy can be targeted for the areas to receive radiotherapy along with a limit of no more than 20% of this value (i.e., 16 Gy) in a critical structure which is likely to be adversely affected by irradiation. The radiotherapy objective also optionally includes constraints on the source parameters, e.g. beam portion intensities can be limited to between a selected minimum intensity (e.g., zero intensity) and a selected maximum intensity corresponding to a maximum output in the beam portion for the radiation source.

With continuing reference to FIG. 1, a radiation delivery sub-system 60 includes a radiation delivery apparatus 62 which has a radiation source 64 mounted on a rotating gantry 66. The gantry 66 rotates a radiation source 64 about an axis of rotation 68. A support 70 rigidly positions the subject with the target area exposed to an intensity-modulated radiation beam 72 produced by the radiation source 64.

In tomotherapy, the support 70 linearly moves the subject while the gantry 66 rotates the radiation source 64 to effectuate a helical orbiting of the radiation source about the subject. The intensity-modulated radiation beam 72, such as a photon beam, has a cross-sectional area 74 with varying intensity and/or perimeter. The radiation beam 72 can be applied continuously during the helical rotation, or can be selectively switched on and off during the radiotherapy.

A suitable radiation source 64 includes a linear electron accelerator or linac which produces an accelerated electron beam. In a preferred embodiment, a tungsten or other target is irradiated by the accelerated electron beam to produce the photon beam 72 of x-rays or gamma rays for photon radiotherapy. Other types of radiation, such as proton beams and neutron beams known to the art, or the accelerated electron beam produced by the linac, are also contemplated to be applied to the subject during the radiation therapy.

Intensity modulation of the radiation beam 72 is suitably obtained using one or more multi-leaved collimators (MLC) 76. As is known to those skilled in the art, an MLC includes an array of individually movable radiation-blocking paired leaves that together define a selectably sized and shaped radiation aperture. Advantageously, the MLC's are controlled to move to define multiple aperture openings for a single radiation source. Although a conventional linac apparatus 62 is shown in FIG. 1, it is contemplated to employ a plurality of non-rotating or step-and-shoot radiation sources to apply several radiation beams simultaneously or consecutively that cross within the target area of the subject. It is also contemplated to use either system for tomotherapy which delivers the radiation by helically orbiting the source about the patient. The multiple-beam system requires complex MLC's to obtain adequate spatial modulation of the combined beam intensity. For tomotherapy, a simple binary fan-beam MLC can replace the conventional cone-beam MLC, since spatial dosage modulation is obtained by opening or closing one leaf (or beamlet) 72 both in space and in time during the helical rotating.

In order to register the radiotherapy with the previously acquired diagnostic images, the fiduciary markers are preferably used. In a suitable embodiment, detectors (not shown) receive low power x-rays produced by the radiation source 64 to effectuate a low-resolution CT imaging which can be used to image the fiduciary markers which were placed on the subject prior to the diagnostic imaging. Optionally, a separate CT scanner, e.g. separate x-ray source and detector array, are integrated with the radiation delivery sub-system 60, in which case the diagnostic imaging can be performed at the radiation delivery sub-system 60 to reduce misregistration between the imaging and the radiotherapy.

With continuing reference to FIG. 1, an inverse planning processor 80 computes an optimized radiation beam intensity modulation for the intensity-modulated radiation beam 72. To optimize the intensity modulation of one or more beams used for radiotherapy, the beams are mathematically divided into a plurality of beamlets whose parameters, such as intensity, are optimized in an iterative manner.

Figure 2:
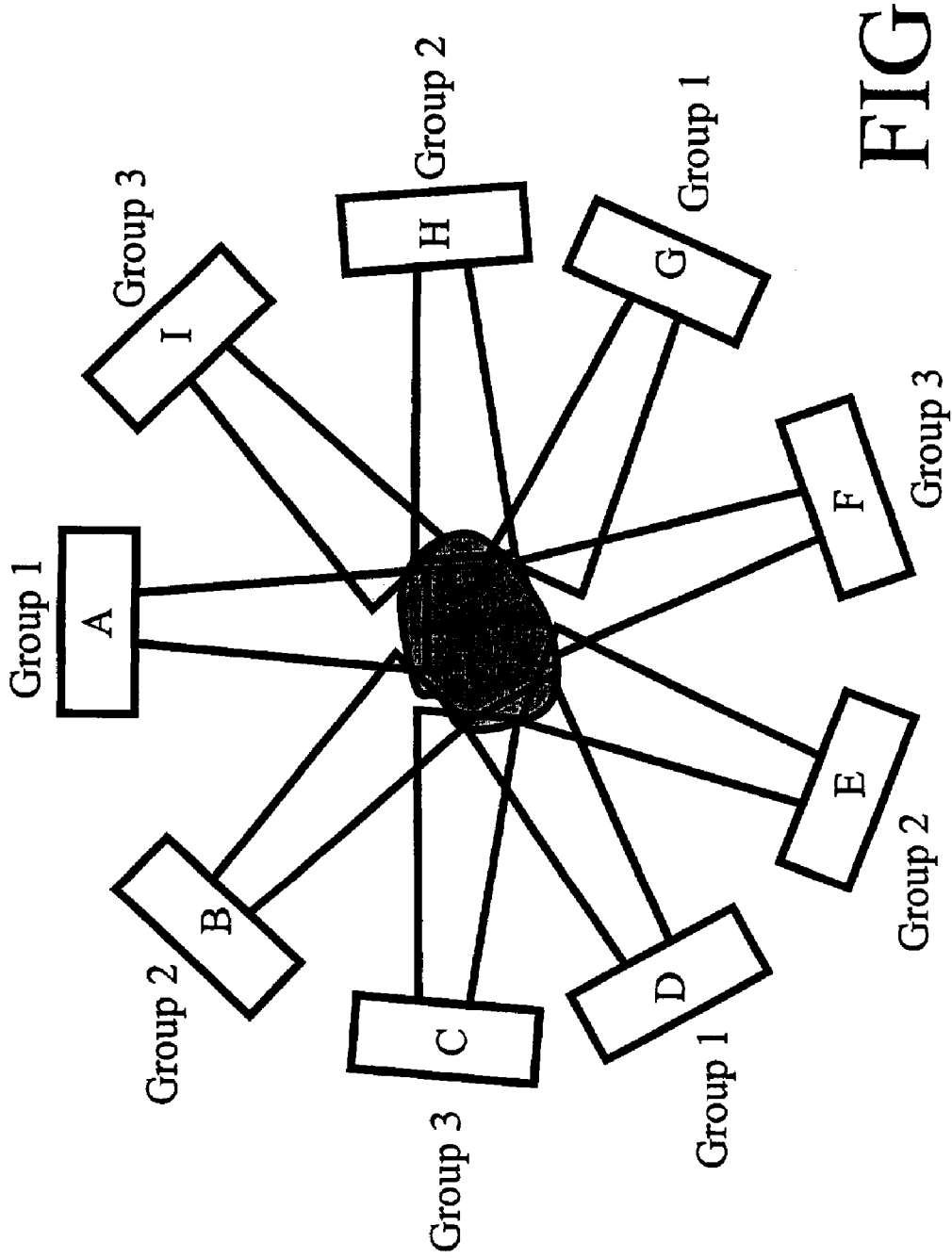
FIG. 2 diagrammatically illustrates an exemplary grouping of the beams of a nine-beam radiotherapy delivery system into three groups for inverse planning of the intensity modulation of the beams.

With reference to FIG. 2, an exemplary multiple-beam radiation delivery apparatus is described. In multiple-beam radiotherapy, multiple crossing beams are applied to the target area typically sequentially to obtain the desired intensity modulation. FIG. 2 diagrammatically shows the radiation beams of an exemplary nine-beam radiation delivery system with the beams arranged in a plane with equal angular separations of 40°. Each beam is mathematically divided into a plurality of beamlets. For example, a 10×10 cm$^2$ beam can be divided into 400 beamlets each having an area of 0.5×0.5 cm$^2$. In a nine-beam system, this corresponds to 3,600 beamlet intensity parameters, assuming that each beamlet angle and orientation is held fixed.

The beams shown in FIG. 2 can be produced sequentially by one or more radiation sources mounted on a rotating gantry operating in a rotational step-and-shoot mode. Furthermore, although only nine beams are shown with a corresponding 3,600 parameters, more beams can be used and/or the beamlet resolution can be increased, resulting in far more parameters. Radiotherapy planning which employs 10,000 or more beamlets is contemplated to provide adequate planning resolution and accuracy in complex multiple-beam radiotherapy procedures. Preferably, the beams are arranged in a non-opposing fashion, i.e. with no two beams positioned at 180° angular separation. It will also be appreciated that, although the nine beams of FIG. 2 are co-planar, use of non-coplanar beams is also contemplated.

With a tomotherapy apparatus, at least one beam is helically rotated during the radiation tomotherapy. The continuously rotating beam is intensity-modulated during the helical rotation, and the temporally intensity-modulated beam can be described by a plurality of virtual beams of short time duration corresponding to a small angular interval of the rotating beam. Each virtual beam is divided into beamlets for optimization of the temporal intensity-modulation of the rotating beam. In present radiation tomotherapy systems upwards of 60,000 beamlet intensity parameters are preferably optimized to adequately resolve and optimize the spatially and temporally modulated beam intensity to be applied during the radiation tomotherapy.

With continuing reference to FIG. 1, because optimization of a large number of beamlet parameters is computationally intense, the parameters are divided into a plurality of groups, e.g. N groups 82, 84, . . . 86. The optimization is performed group-by-group in a cumulative manner. For example, assuming that the N parameter groups include equal numbers of beamlets with equal intensities, the first parameter group 82 is preferably optimized respective to the radiation treatment objective produced by the contouring processor 54 but weighted by a scaling factor of 1/N since the beamlets of the first group 82 are expected to provide only 1/Nth of the total radiation. The second group 84 is then optimized respective to the radiation treatment objective scaled by a factor of (2/N), using the simulated radiation produced by beamlets of the first group 82 (whose parameters are now fixed) combined with the simulated radiation produced by beamlets of the second group 84 whose values are currently being optimized. This process continues until the Nth group 86 is optimized relative to the full radiation treatment objective (i.e., scaled by a scaling factor of N/N=1) while the parameter values of the other N−1 groups are held constant.

Alternately, each of the N groups can be scaled by 1/N and optimized independently of the other groups. The N intensities at each position are then summed. However, this optimization method disadvantageously can produce cumulative intensity errors which are reduced by optimizing the groups successively and including simulated radiation produced by the previously optimized parameters in the optimization of the current parameter group.

A preferred grouping of beamlets is described in greater detail with reference to FIG. 2, which diagrammatically shows the radiation beams of an exemplary nine-beam radiation delivery system with the beams arranged in a plane with equal angular separations of 40°. To reduce biasing of optimization of the beamlet parameters due to the group-by-group optimization, the beamlets are preferably divided such that each beam has all its component beamlets in a single group. Furthermore, the beams in each group are preferably selected such that the beams are maximally angularly separated. In the exemplary nine-beam system shown in FIG. 2, a first group 1 includes the beams designated A, D, and G; a second group 2 includes the beams designated B, E, and H; and a third group 3 includes the beams designated C, F, and I. It will be appreciated that the three beams in each group are separated by 120°, which corresponds to a maximal angular separation of the beams in each group for this nine-beam configuration. Each group preferably is assigned a weighting factor of ⅓, assuming each of the nine beams have the same area and are divided into equal numbers of beamlets.

In the examples of FIGS. 1 and 2, the number of beamlets in each group was the same. If some groups contain more beamlets, the weightings of the groups is preferably adjusted accordingly. For three groups in which the first group has 2,000 beamlets while the second and third groups each have 1,000 beamlets, preferred weightings would be 0.5 for the first group of 2,000 beamlets and 0.25 for each of the second and third groups each having 1,000 beamlets. Such a situation can arise with a multi-beam system in which beams with different areas are combined to effectuate the radiotherapy.

With returning reference to FIG. 1, the inverse planning processor 80 computes optimized beamlet parameters, e.g. optimized beamlet intensities, which describe an intensity modulation of the radiotherapy beams that will closely correspond with the radiation treatment objective. A conversion processor 90 converts the beamlet intensities into control parameters for the radiation delivery sub-system 60, such as selected temporally varying settings for the MLC 76 of the radiation delivery apparatus 62. A radiation delivery apparatus controller 92 controls the radiation delivery sub-system 60 to deliver the selected radiation therapy.

Figure 3:
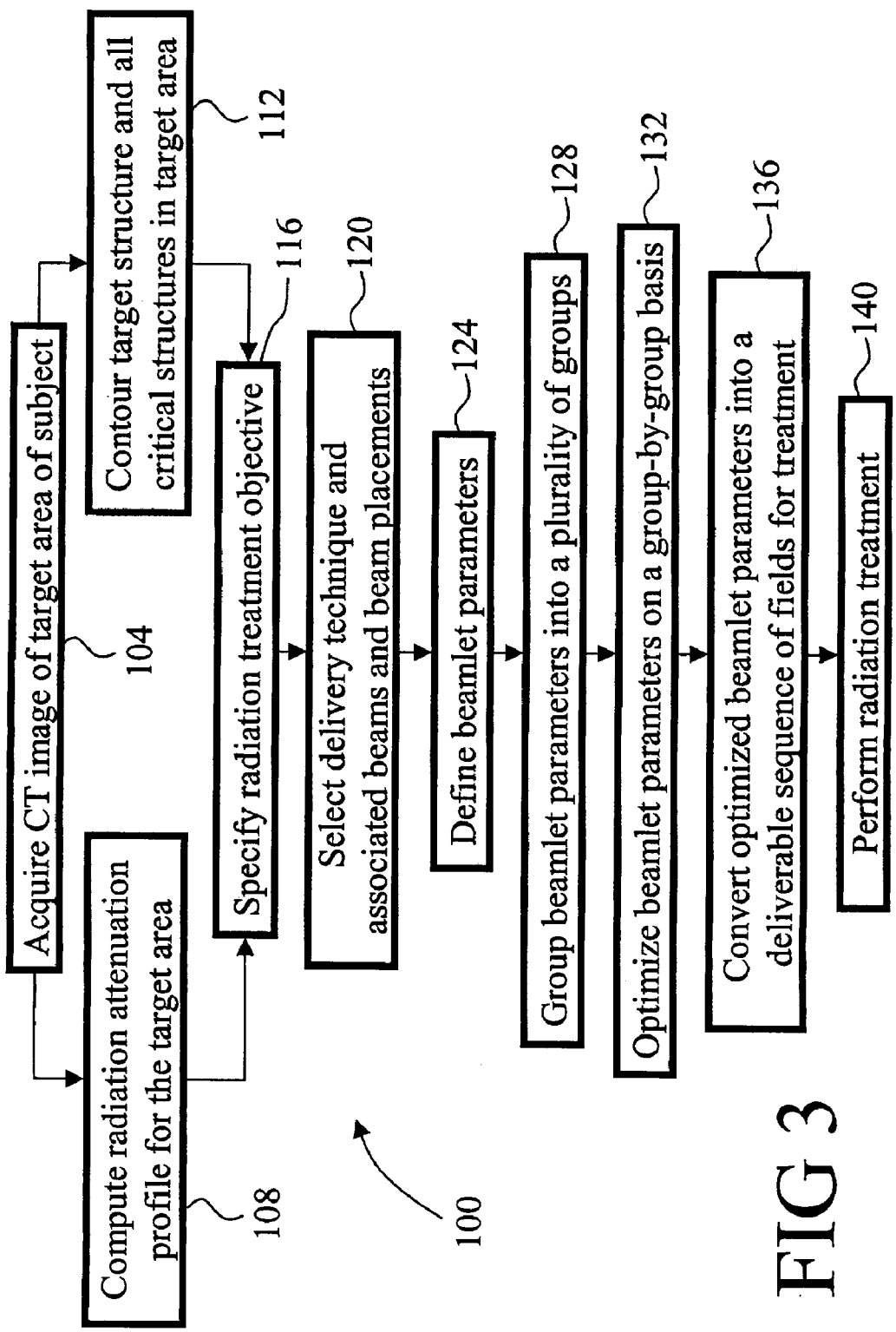
FIG. 3 diagrammatically illustrates a method for performing a selected radiation therapy in accordance with an embodiment of the invention.

With reference to FIG. 3, a method 100 for performing radiation therapy on a subject is described. Diagnostic images are acquired in a step 104, using CT, PET, or another imaging modality 12. A radiation attenuation profile is computed by the density profiling processor 50 based on the diagnostic images in a step 108. The radiation attenuation profile corresponds to the type of radiation used in the radiotherapy. For photon-based radiotherapy and CT diagnostic imaging, the attenuation coefficients are substantially similar for the x-rays of the CT scanning and the photons of the radiotherapy, which minimizes the use of correction factors or the like in estimating the attenuation profile for the photon radiotherapy.

When the radiation used in the medical imaging differs substantially in absorption properties from the radiation used in the radiotherapy, suitable conversion parameters are preferably employed. In a suitable attenuation conversion for a human subject, attenuation coefficients for bone, fat, and other tissues types are assigned to anatomical structures identified in the diagnostic images based on identification of the tissue type of each structure.

The target structure or structures for the radiotherapy are contoured by the contouring processor 54 in a step 112, along with any critical structures within the target area for which radiation exposure is to be minimized. In a suitable embodiment, the contouring 112 includes user input at the console 52 via interactive images or image renderings produced from the diagnostic imaging step 104. Optionally, the contouring 112 is integrated with the step 108 of computing of the radiation profile, since the tissue type of each contoured areas is conveniently identified during the contouring and assigned a corresponding attenuation coefficient.

A radiation treatment objective is specified by the operator or with reference to a look-up table in a step 116. Typically, the treatment objective includes a target radiation dosage in each target structure and optimal bounds (minimum and/or maximum dosages) for each target structure. The treatment objective can also include bounds in critical structures, which typically are maximum dosage bounds that protect the critical structure or structures from excessive radiation exposure. The treatment objective can also include bounds on the intensity output of the beams, for example corresponding to the intensity level range that a radiation source is capable of producing.

The radiotherapy delivery technique and associated beams and beam placements is selected by the user in a step 120 based on the type of radiation therapy and the type of radiation delivery apparatus 60 to be used. For a multi-beam radiation delivery system such as is schematically shown in FIG. 2, the beam selection corresponds with the discrete radiation sources or with the plurality of beam positions in the step-and-shoot radiotherapy sequence. For tomotherapy, the continuously helically rotating beam is approximated by a plurality of stationary beams of short duration corresponding to small angular intervals of the helically rotating beam.

The beamlet parameters are defined in step 124. Each beam is divided into a plurality of beamlets, also called bixels, whose intensities represent the intensity-modulation of the beam. For example, a 10×10 $cm^2$ beam can be divided into 400 0.5×0.5 $cm^2$ beamlets which cover the cross-sectional area of the 10×10 $cm^2$ beam. Typically, the beamlet parameters includes the intensity of each beamlet. However, other beamlet parameters are also contemplated, such as the beamlet application time, the beamlet angle, and so forth.

As discussed previously, the beamlet parameters typically number in the thousands or tens of thousands. To improve the computational efficiency of the optimization of the beamlet parameters, the beamlet parameters are grouped into a plurality of groups in a step 128. Preferably, the beamlet parameters for each beam are included in a single group, and the beams within each group are preferably maximally angularly separated.

The beamlet parameters are optimized on a group-by-group basis in step 132. The optimized beamlets are converted into a deliverable sequence of fields in step 136. This conversion can include selecting leaf-pair aperture settings for one or more MLC's, selecting a slit collimator opening, and the like. For radiation tomotherapy, the conversion includes computing the temporal variation of the MLC settings or slit openings based on the virtual beams representative of angular intervals of the rotating beam. A radiation delivery apparatus performs the deliverable fields sequence to effectuate the radiation therapy.

Figure 4:
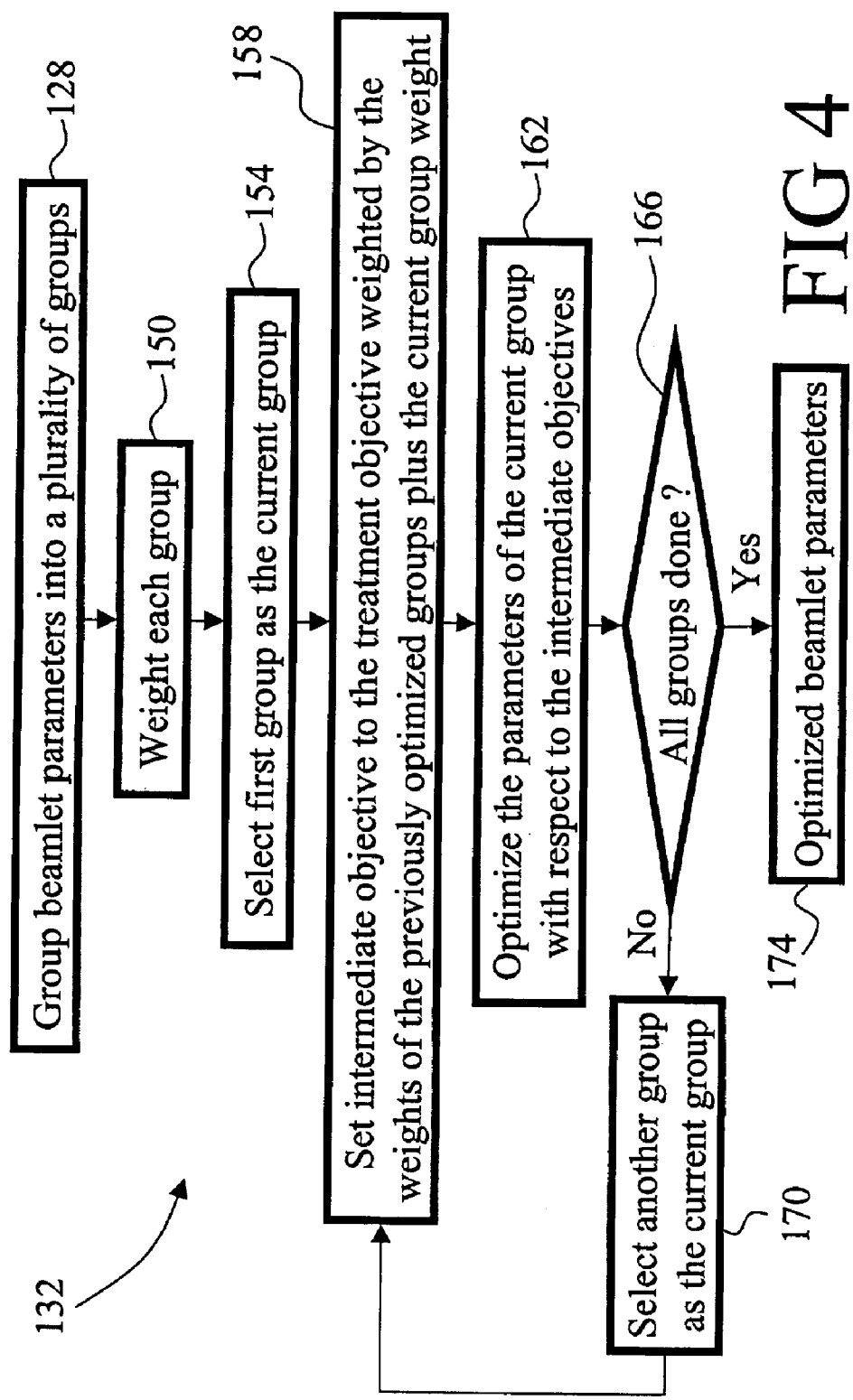
FIG. 4 diagrammatically illustrates a suitable method for performing the beamlet parameters optimization on a group-by-group basis.

With reference to FIG. 4, a suitable method for performing the step 132 of optimizing the beamlet parameters on a group-by-group basis is described. Each group is assigned a contribution weight in a step 150. For uniform groupings in which each group includes an equal number of beamlets, the contribution weight is typically 1/N where N is the number of groups.

For non-uniform groupings the contribution weight is preferably assigned as a ratio of the number of beamlets in the group divided by the total number of beamlet parameters (which reduces to 1/N for a uniform grouping). For example, if 50,000 beamlets are grouped into three groups of 16,000 beamlets, 14,000 beamlets, and 20,000 beamlets, the respective group weightings are selected as 16,000/50,000=0.32, 14,000/50,000=0.28, and 20,000/50,000=0.4. It will be appreciated that for either uniform or non-uniform groupings the total of the weights of all the groups adds up to one.

The groups are then iteratively processed, starting by selecting a first group as the current group in step 154. An intermediate radiation dosage distribution objective is selected in step 158 as the radiation treatment objective weighted by the weighting of the first group. The first group is optimized respective to the intermediate radiation dosage distribution objective in step 162. An iterative least squares minimization is suitably applied in the step 162, using a figure of merit such as:

$$\text{figure of merit} = \sum_{i} (D_i - D_{obj})^2 \quad (1)$$

where the index i goes over all voxels of the region of interest of the subject, $D_i$ is the simulated dosage at the ith voxel computed using the beamlet parameters of the current iteration, and $D_{obj}$ is the radiation dosage of the ith voxel of the intermediate radiation dosage distribution objective. However, those skilled in the art will recognize that the least-squares figure of merit is exemplary only, and will further recognize that other suitable figures of merit can be substituted therefor.

The least squares optimization is suitably performed using a quasi-Newton gradient-based iterative optimization method which minimizes the figure of merit to bring the simulated dosage $D_i$ optimally close to the objective dosage $D_{obj}$ in the region of interest. However, those skilled in the art will recognize that the quasi-Newton gradient-based method is exemplary only, and will further recognize that other suitable parameter optimization methods can be substituted therefor.

A decision step 166 recognizes that there are additional groups to be optimized, and another group is selected as the current group in a step 170. The step 158 computes a new intermediate radiation dosage distribution objective as the radiation treatment dosage objective weighted by the combined weights of the current group and all previously optimized groups. It will be recognized that this amounts to increasing or scaling up the intermediate radiation dosage distribution objective by the weight of the current group selected in the step 170.

The step 162 optimizes only the current group parameters respective to the increased intermediate radiation dosage distribution objective. The figure of merit of equation (1) is still used; however, the simulated dosage $D_i$ includes contributions of the beamlets of the previously optimized groups (e.g., the first group selected in the step 154) combined with contributions of the beamlets of the currently optimized group which was selected in the step 170. However, the quasi-Newton gradient-based iterative optimization method only optimizes the parameters of the current group selected in the step 170. Beamlet parameters of the previously optimized groups such as the first group selected in the step 154 are not optimized, since they were optimized during the previous iteration.

The decision step 166 and the group selection step 170 iterate through the groups, each time increasing the intermediate radiation dosage distribution objective through the step 158 according to the weight of the new current group and optimizing only the beamlet parameters of the current group in the step 162 respective to the figure of merit of equation (1) which includes contributions to the simulated dosage $D_i$ from both beamlets of the current group and beamlets of the previously optimized groups.

When the decision step 166 reaches the (N−1)th group, the selection step 170 selects the last (Nth) group for optimization. In this last loop iteration, the step 158 computes the intermediate radiation dosage distribution objective in the usual way as the radiation treatment objective weighted by the combined weights of all previously optimized groups plus the current group. In this last (Nth) iteration, however, the combined weights equal one, since the groups were weighted in the step 150 such that the sum of all the weights equals one. Hence, in the last iteration the intermediate radiation dosage distribution objective equals the radiation treatment objective. The last group is optimized in the step 162 respective to the radiation treatment objective, with the simulated radiation dosage including contributions from all the beamlets in all the groups, but as usual the quasi-Newton gradient-based iterative optimization method optimizes only beamlet parameters of the current, i.e. last (Nth) group.

Once this last iteration optimizes the beamlet parameters of the last (Nth) group in the step 162, the decision step 166 recognizes that there are no further groups to be optimized, and that the beamlet parameters in all the groups collectively correspond to the optimized beamlet parameters 174.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method for delivering to a subject a selected radiation treatment described by a treatment radiation dosage distribution objective, the delivering including application of at least one intensity-modulated beam whose radiation output is described by a plurality of beamlet parameters, the method comprising:

(a) dividing the beamlet parameters into a plurality of groups, each group including one or more beamlet parameters;

(b) assigning a group weighting for each group based at least on a fraction of the beamlet parameters included in the group;

(c) selecting a first group;

(d) computing a first intermediate radiation dosage distribution objective based on the treatment radiation dosage distribution objective and the first group weighting;

(e) optimizing the first group of beamlet parameters respective to the first intermediate radiation dosage distribution objective;

(f) selecting a next group;

(g) determining a second intermediate radiation dosage distribution objective based on the treatment radiation dosage distribution objective and the next group weighting;

(h) optimizing the next group of beamlet parameters respective to the second intermediate radiation dosage distribution objective;

(i) repeating the steps (f)–(h) to optimize all the beamlet intensity parameters;

(j) converting the optimized beamlet intensity parameters to a deliverable sequence of radiation fields; and (k) applying the at least one intensity-modulated beam to effectuate the deliverable sequence.

2. The method as set forth in claim 1, wherein the at least one intensity-modulated beam includes at least two beam orientations and the dividing step (a) includes:

dividing the beamlet parameters into a plurality of groups such that the beamlet parameters associated with each beam orientation are included in a single group.

3. The method as set forth in claim 2, wherein the dividing step (a) further includes:

dividing the beamlet parameters associated with each beam orientation into a single group such that the beams in each group are maximally spatially separated.

4. The method as set forth in claim 1, wherein the step (d) of computing a first intermediate radiation dosage distribution objective includes:

initializing the intermediate radiation dosage distribution objective as the treatment radiation dosage distribution objective multiplied by the first group weighting.

5. The method as set forth in claim 4, wherein the step (g) of determining a second intermediate radiation dosage distribution objective includes:

increasing the first intermediate radiation dosage distribution objective by the treatment radiation dosage distribution objective multiplied by the next group weighting.

6. The method as set forth in claim 5, wherein the step (b) of assigning a group weighting includes:

assigning a group weighting as a number of beamlet parameters included in the group divided by a total number of beamlet parameters in all the groups.

7. The method as set forth in claim 1, wherein the step (b) of assigning a group weighting includes:

assigning a group weighting as a number of beamlet parameters included in the group divided by a total number of beamlet parameters in all the groups.

8. The method as set forth in claim 1, wherein the step (e) of optimizing the first group of beamlet parameters includes:

computing a simulated radiation dosage distribution based on the first group of beamlet parameters; and iteratively optimizing the first group of beamlet parameters such that the simulated radiation dosage distribution substantially conforms to the first intermediate radiation dosage distribution objective.

9. The method as set forth in claim 1, wherein the step (h) of optimizing the next group of beamlet parameters includes:

computing a first simulated radiation dosage distribution based on previously optimized groups of beamlet parameters;

computing a second simulated radiation dosage distribution based on the next group of beamlet parameters;

combining the first and second simulated dosage distributions to obtain a total simulated radiation dosage distribution; and iteratively optimizing the next group of beamlet parameters such that the total simulated radiation dosage distribution substantially comports with the second intermediate radiation dosage distribution objective.

10. The method as set forth in claim 1, wherein the optimizing steps (e) and (h) include:

constraining the optimizing by a radiation dosage limit for a selected portion of the subject.

11. The method as set forth in claim 1, wherein step (j) of converting the optimized beamlet intensity parameters to a deliverable sequence of radiation fields includes computing parameters of a multi-leaved collimator such that the collimator output is representative of the optimized beamlet parameters.

12. The method as set forth in claim 1, wherein step (k) of applying at least one intensity-modulated beam to effectuate the deliverable sequence includes one of:

applying a plurality of intensity-modulated beams to the subject substantially simultaneously, applying an intensity-modulated beam to the subject continuously as the beam rotates about the subject, and applying an intensity-modulated beam to the subject in sequential radiation pulses as the beam moves through a series of angular orientations about the subject.

13. The method as set forth in claim 1, wherein the beamlet parameters include:

beamlet intensities, wherein the beamlets combine to represent the at least one intensity-modulated beam.

14. A radiation treatment apparatus for delivering a radiation treatment to a subject, the radiation treatment apparatus comprising:

a diagnostic imaging scanner that acquires a diagnostic image of a target area of the subject;

a contouring processor that computes a radiation treatment objective based on the diagnostic image;

a radiation delivery apparatus configured to deliver the radiation treatment objective to the subject, the radiation produced by the radiation delivery apparatus during the radiation treatment representable as a plurality of parameterized beamlets;

an inverse planning processor that computes beamlet parameters conforming with the radiation treatment objective, the inverse planning processor performing a method including:

grouping the beamlet parameters into a plurality of groups each including one or more beamlet parameters, assigning a contribution weight to each beamlet parameter group, optimizing a first beamlet parameter group with respect to a first intermediate target dosage objective corresponding to the radiation treatment objective weighted by the contribution weight of the first beamlet parameter group, and optimizing successive beamlet parameter groups with respect to a second intermediate target dosage objective corresponding to the radiation treatment objective weighted by the contribution weight of at least the currently optimized beamlet parameter group; and a conversion processor that converts the optimized beamlet parameters into configuration parameters of the radiation delivery apparatus.

15. The radiation treatment apparatus as set forth in claim 14, wherein the diagnostic imaging scanner includes:

a computed tomography scanner including an x-ray source mounted on a rotating gantry and an x-ray receiver array arranged to receive radiation produced by the x-ray source.

16. The radiation treatment apparatus as set forth in claim 14, wherein the radiation delivery apparatus includes one of:

a radiation source mounted on a rotating gantry that rotates the radiation source about the target area of the subject, wherein the plurality of parameterized beamlets represent radiation produced by the rotating radiation source over a selected time interval, and one or more radiation sources that produce beams at selected beam orientations spaced around the target area of the subject, wherein the plurality of parameterized beamlets represent radiation produced by the one or more radiation sources.

17. The radiation treatment apparatus as set forth in claim 14, wherein the radiation delivery apparatus includes a tomotherapy apparatus delivering a beam of radiation to the subject from a radiation aperture that helically orbits the subject.

18. The radiation treatment apparatus as set forth in claim 14, wherein the radiation delivery apparatus delivers one of: x-rays, gamma radiation, proton radiation, and neutron radiation.

19. The radiation treatment apparatus as set forth in claim 14, wherein the radiation delivery apparatus includes a multi-leaved collimator that produces an intensity-modulated radiation beam.

20. The radiation treatment apparatus as set forth in claim 14, wherein the step of optimizing successive beamlet parameter groups performed by the inverse planning processor includes:

(a) computing a simulated radiation distribution of the previously optimized and currently optimized beamlet parameter groups;

(b) comparing the simulated radiation distribution with the second intermediate target dosage objective which corresponds to the radiation treatment objective weighted by the combined contribution weights of the previously optimized and currently optimized beamlet parameter groups;

(c) estimating improved parameter values for the currently optimized beamlet parameter group while holding the parameter values for the previously optimized beamlet parameter groups unchanged; and (d) iteratively repeating the computing, comparing, and estimating steps (a), (b), and (c) to iteratively optimize the currently optimized beamlet parameter group.

21. An apparatus for delivering to a subject a selected radiation treatment described by a treatment radiation dosage distribution objective, the delivering including application of at least one intensity-modulated beam whose radiation output is described by a plurality of beamlet parameters, the method comprising:

a grouping means for dividing the beamlet parameters into a plurality of groups, each group including one or more beamlet parameters;

a weighting means for assigning a group weighting for each group based at least on a fraction of the beamlet parameters included in the group;

a means for computing an intermediate radiation dosage distribution objective based on the treatment radiation dosage distribution objective and combined weightings of one or more selected groups;

an optimizing means for optimizing the beamlet parameters of a current group respective to the intermediate radiation dosage distribution objective;

a looping means for successively applying the means for computing an intermediate radiation dosage distribution objective and the optimizing means to determine optimized values for the beamlet parameters of each group;

a converting means for converting the optimized beamlet intensity parameters to a deliverable sequence of radiation fields; and a radiation delivery means for applying the at least one intensity-modulated beam to effectuate the deliverable sequence.

* * * * *